(12) United States Patent
Lee et al.

(10) Patent No.: US 11,553,868 B2
(45) Date of Patent: Jan. 17, 2023

(54) ECG DATA DISPLAY METHOD FOR DETECTION OF MYOCARDIAL ISCHEMIA

(71) Applicants: Hyun Ok Lee, Seoul (KR); Kyeong Hwan Cha, Seoul (KR); Jong Hyeok Kim, Seoul (KR)

(72) Inventors: Hyun Ok Lee, Seoul (KR); Kyeong Hwan Cha, Seoul (KR); Jong Hyeok Kim, Seoul (KR)

(73) Assignee: BIONET CO., LTD, Seoul (KR)

( * ) Notice: Subject to any disclaimer, the term of this patent is extended or adjusted under 35 U.S.C. 154(b) by 0 days.

(21) Appl. No.: 17/224,086

(22) Filed: Apr. 6, 2021

(65) Prior Publication Data

US 2021/0338133 A1 Nov. 4, 2021

(30) Foreign Application Priority Data

Apr. 29, 2020 (KR) .......................... 10-2020-0052056

(51) Int. Cl.
*A61B 5/339* (2021.01)
*A61B 5/358* (2021.01)
*A61B 5/28* (2021.01)

(52) U.S. Cl.
CPC ................ *A61B 5/339* (2021.01); *A61B 5/28* (2021.01); *A61B 5/358* (2021.01)

(58) Field of Classification Search
CPC ................................. A61B 5/358; A61B 5/339
See application file for complete search history.

(56) References Cited

U.S. PATENT DOCUMENTS

| 8,725,255 B2* | 5/2014 | Arcot-Krishnamurthy ................. A61N 1/365 607/9 |
| 2013/0231578 A1 | 9/2013 | Takayanagi et al. |
| 2013/0324870 A1* | 12/2013 | Rajagopalan .......... A61B 5/349 600/523 |
| 2014/0039338 A1* | 2/2014 | Nelwan ................. A61B 5/341 600/523 |
| 2016/0135703 A1 | 5/2016 | Zhang |

FOREIGN PATENT DOCUMENTS

| WO | 2009077915 A1 | 6/2009 |
| WO | 2010037400 A1 | 4/2010 |
| WO | 2010099386 A1 | 9/2010 |
| WO | 2011089488 A1 | 7/2011 |

* cited by examiner

*Primary Examiner* — George R Evanisko
(74) *Attorney, Agent, or Firm* — John K. Park; Park Law Firm

(57) ABSTRACT

Provided is a method for displaying electrocardiogram (ECG) data for the detection of myocardial ischemia, wherein a map is configured in the form of concentric circles using ST segments obtained through ECG measurement such that the inner circle consists of a "depression" origin and the outer circle consists of an "elevation" origin so as to display by connecting graphs or dots according to the measured ECG values of limb leads (frontal plane leads; I to aVF) and chest leads (precordial plane leads; V1 to V6), and the intuitive confirmation of the presence of subendocardial ischemia or transmural injury is enabled through the map, thereby making it possible to quickly and accurately recognize the patient's conditions and inducing prompt treatment.

14 Claims, 9 Drawing Sheets

# ECG DATA DISPLAY METHOD FOR DETECTION OF MYOCARDIAL ISCHEMIA

BACKGROUND OF THE DISCLOSURE

Field of the Disclosure

The present disclosure relates to a method for displaying electrocardiogram (ECG) data for the detection of myocardial ischemia, and more specifically, to a method for displaying ECG data for the detection of myocardial ischemia, in which a map is configured in the form of concentric circles using ST segments obtained through ECG measurement such that the inner circle consists of a "depression" origin and the outer circle consists of an "elevation" origin so as to display by connecting graphs or dots according to the measured ECG values of limb leads (frontal plane leads; I to aVF) and chest leads (precordial plane leads; V1 to V6), and the intuitive confirmation of the presence of subendocardial ischemia or transmural injury is enabled through the map, thereby making it possible to quickly and accurately recognize the patient's conditions and inducing prompt treatment.

In general, an electrocardiogram (hereinafter, ECG) is an action current according to the contraction and expansion of the heart muscle, which is measured and recorded by attaching an electrode thereto from the outside. The action potential generated when the heart muscle contracts and relaxes causes an electric current that spreads from the heart to the whole body, and this current generates a potential difference depending on the position of the body. This potential difference can be detected and recorded through a surface electrode attached to the human skin. Such an ECG is used to check if there is any abnormality in the heart, and it is very important because it is used as a basic method for diagnosing heart system diseases (e.g., myocardial ischemia, myocardial infarction, arrhythmia, etc.).

The myocardial ischemia is a major complication of cardiac function and is considered a major cause of myocardial infarction and cardiac arrhythmia. At the cellular level, the main characteristic of myocardial ischemia may appear as a decline or elevation of the ST segments in the ECG. In a method of detecting myocardial ischemia episodes, conventional techniques are based on a method of detecting myocardial ischemia (episodes) and a method of detecting based on each and every heart rate.

The "method for detecting myocardial ischemia using comparison analysis of characteristics in the time and frequency domains of heart rate variability" has been published as Korean Patent No. 10-1273652 (hereinafter, "Patent Document 1").

Referring to Patent Document 1, the conventional method for detecting myocardial ischemia is a method of detecting myocardial ischemia using comparison analysis of characteristics in time and frequency domains of heart rate variability, which is characterized by including the following steps: (1) a step of training a neural network based on a weighted fuzzy membership function using a data set for learning a neural network; (2) a step of constructing a classification model in a time domain and a classification model in a frequency domain, based on the weighted fuzzy membership function-based neural network learned in Step (1); and (3) a step of detecting the presence of myocardial ischemia from a patient data by applying the patient data set, from which the presence of myocardial ischemia is to be detected, to the classification model in the time domain and the classification model in the frequency domain constructed in Step (2).

Patent Document 1 consisting of such a constitution, in which myocardial ischemia is detected using comparison analysis of characteristics in time and frequency domains of heart rate variability, is configured to reduce the amount of data required for data construction in the myocardial ischemia detection method and reduce the time required for detection of myocardial ischemia, thereby making it capable of effectively detecting myocardial ischemia. However, since it is not easy for the user to intuitively check the presence of a subendocardial ischemia or transmural injury, there was a problem in that it is difficult to promptly and accurately recognize the patient's conditions and perform rapid treatment.

PRIOR ART DOCUMENTS

Patent Documents

Patent Document 1: KR Patent No. 10-1273652

DISCLOSURE OF THE INVENTION

Technical Problem

The present disclosure was designed to solve the above-described problems, and an object of the present disclosure provides a method for displaying electrocardiogram (ECG) data for the detection of myocardial ischemia, in which a map is configured in the form of concentric circles using the ST segments obtained through ECG measurement such that the inner circle consists of a "depression" origin and the outer circle consists of an "elevation" origin so as to display by connecting the graphs or dots according to the measured ECG values of limb leads (frontal plane leads; I to aVF) and chest leads (precordial plane leads; V1 to V6), and the intuitive confirmation of the presence of subendocardial ischemia or transmural injury is enabled through the map, thereby making it possible to quickly and accurately recognize the patient's conditions and inducing prompt treatment.

Technical Solution

To solve the above problems, the method for displaying ECG data for the detection of myocardial ischemia according to a preferred embodiment of the present disclosure is characterized in that a map is configured in the form of concentric circles using the ST segments obtained through ECG measurement such that the inner circle consists of a "depression" origin and the outer circle consists of an "elevation" origin, wherein the measured ECG values of limb leads (frontal plane leads; I to aVF) and chest leads (precordial plane leads; V1 to V6) are displayed from the inner circle in the case of "depression" while the measured ECG values of limb leads (frontal plane leads; I to aVF) and chest leads (precordial plane leads; V1 to V6) are displayed from the outer circle in the case of "elevation".

Additionally, the method is characterized in that five graduated rulers are displayed in the form of concentric circles so as to enable the confirmation of the measured ECG values of limb leads (frontal plane leads; I to aVF) and chest leads (precordial plane leads; V1 to V6) between the inner circle and the outer circle, wherein in the case of "depression", the map is configured to sequentially display the measured values from −1 to −6 from the next adjacent circle to the outer circle with the inner circle as the reference point; and in the case of "elevation", the map is configured to sequentially display the measured values from 1 to 6 from the next adjacent circle to the inner circle with the outer circle as the reference point.

Additionally, the method is characterized in that the map is configured to display a bar graph according to the measured ECG values of limb leads (frontal plane leads; I to aVF) and chest leads (precordial plane leads; V1 to V6), or is configured to display by marking dots on the baseline followed by connecting each dot.

Additionally, the method is characterized in that the map is configured to display the shape of the ventricle inside the inner circle so as to enable the intuitive confirmation of the location of subendocardial ischemia or transmural injury.

Additionally, the method is characterized in that the map is configured such that each measured value is displayed under each lead name, which indicates the measured ECG values of limb leads (frontal plane leads; I to aVF) and chest leads (precordial plane leads; V1 to V6).

DESCRIPTION OF EXEMPLARY EMBODIMENTS

Figure 1:
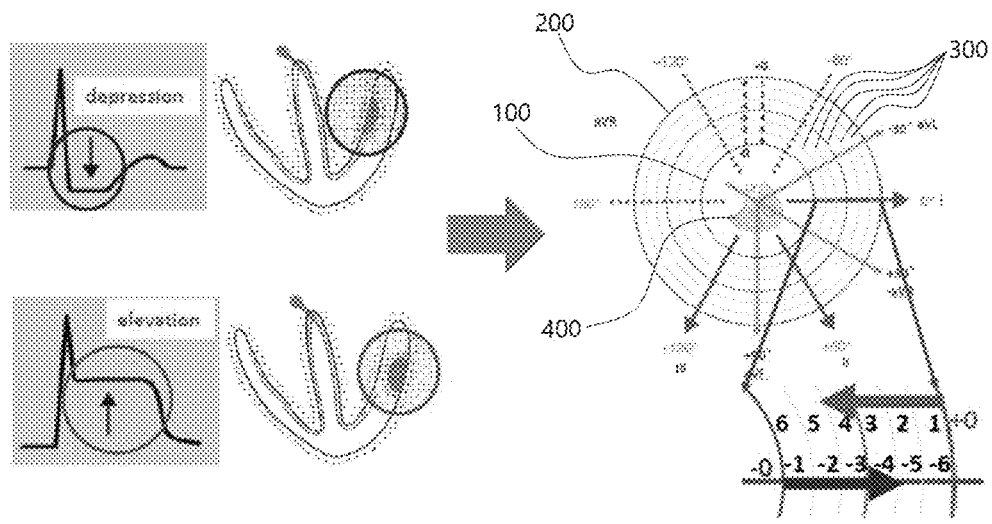
FIG. 1 is an explanatory diagram which shows a method for displaying ECG data for the detection of myocardial ischemia according to a preferred embodiment of the present disclosure.

Hereinafter, the present disclosure will be described in detail with reference to the drawings. The same reference numerals in each drawing indicate the same member.

Figure 2:
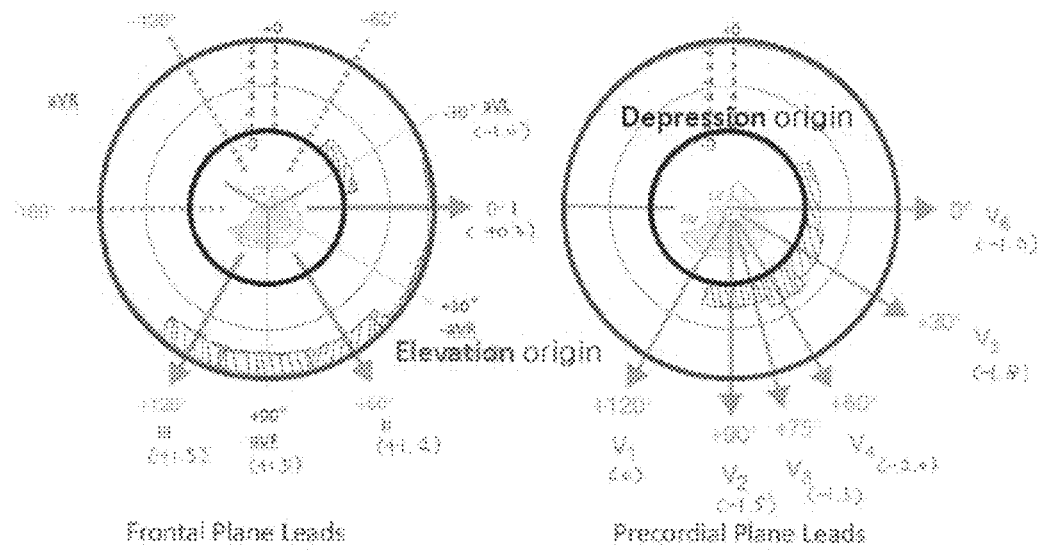
FIG. 2 is an explanatory diagram which shows a state of a method for displaying ECG data for the detection of myocardial ischemia according to a preferred embodiment of the present disclosure, in which the "depression" origin and "elevation" origin are displayed.
Figure 3:
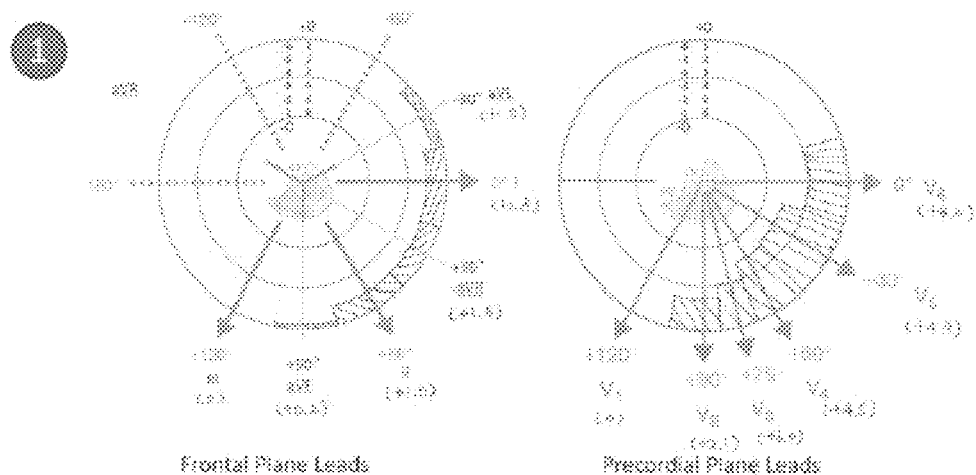
FIG. 3 is an explanatory diagram which shows a state of a method for displaying ECG data for the detection of myocardial ischemia according to a preferred embodiment of the present disclosure, in which the measured ECG values of limb leads (frontal plane leads; I to aVF) and chest leads (precordial plane leads; V1 to V6) are displayed as a bar graph.

FIG. 1 is an explanatory diagram which shows a method for displaying ECG data for the detection of myocardial ischemia according to a preferred embodiment of the present disclosure; FIG. 2 is an explanatory diagram which shows a state of a method for displaying ECG data for the detection of myocardial ischemia according to a preferred embodiment of the present disclosure, in which the "depression" origin and "elevation" origin are displayed; and FIG. 3 is an explanatory diagram which shows a state of a method for displaying ECG data for the detection of myocardial ischemia according to a preferred embodiment of the present disclosure, in which the measured ECG values of limb leads (frontal plane leads; I to aVF) and chest leads (precordial plane leads; V1 to V6) are displayed as a bar graph.

Figure 4:
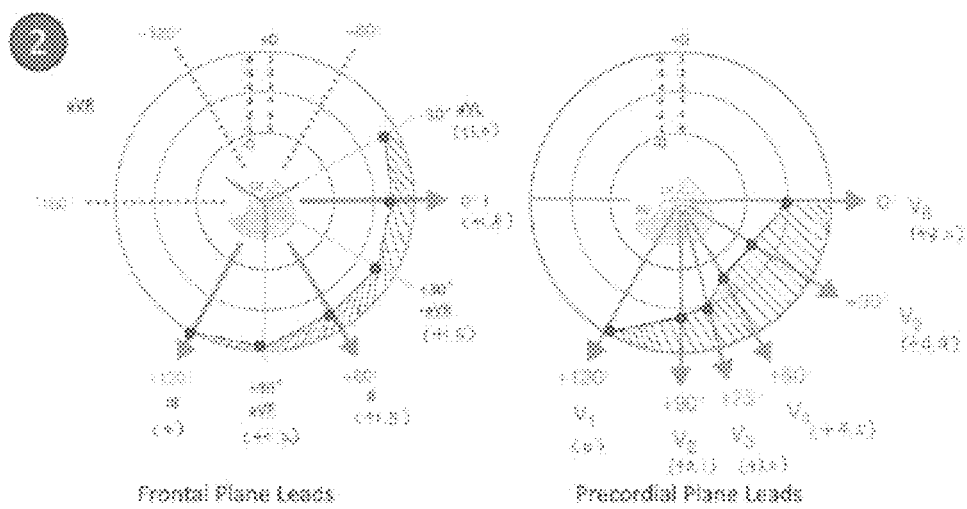
FIG. 4 is an explanatory diagram which shows a state of a method for displaying ECG data for the detection of myocardial ischemia according to a preferred embodiment of the present disclosure, in which the measured ECG values of limb leads (frontal plane leads; I to aVF) and chest leads (precordial plane leads; V1 to V6) are displayed by marking dots on the baseline followed by connecting each dot.
Figure 5:
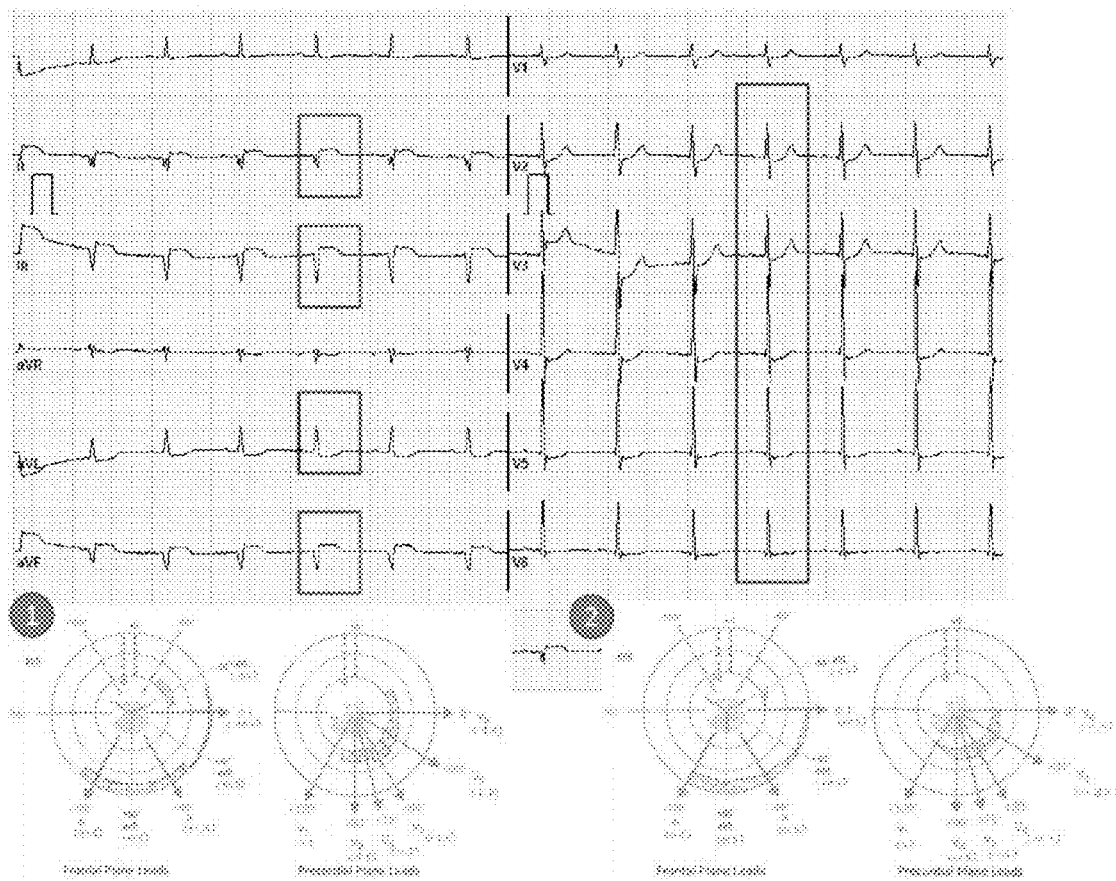
FIGS. 5 to 11 are explanatory diagrams which show various embodiments, with regard to subendocardial ischemia or transmural injury, of a method for displaying ECG data for the detection of myocardial ischemia according to a preferred embodiment of the present disclosure.
Figure 6:
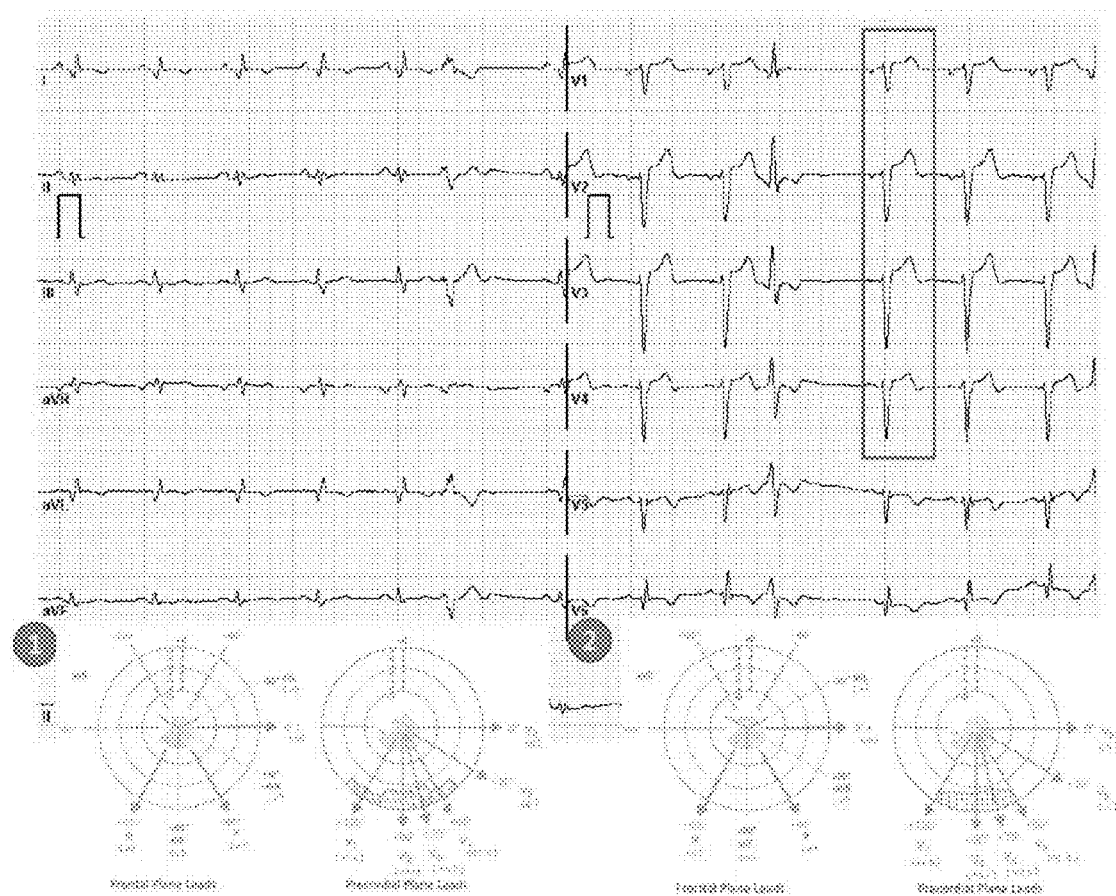
Figure 7:
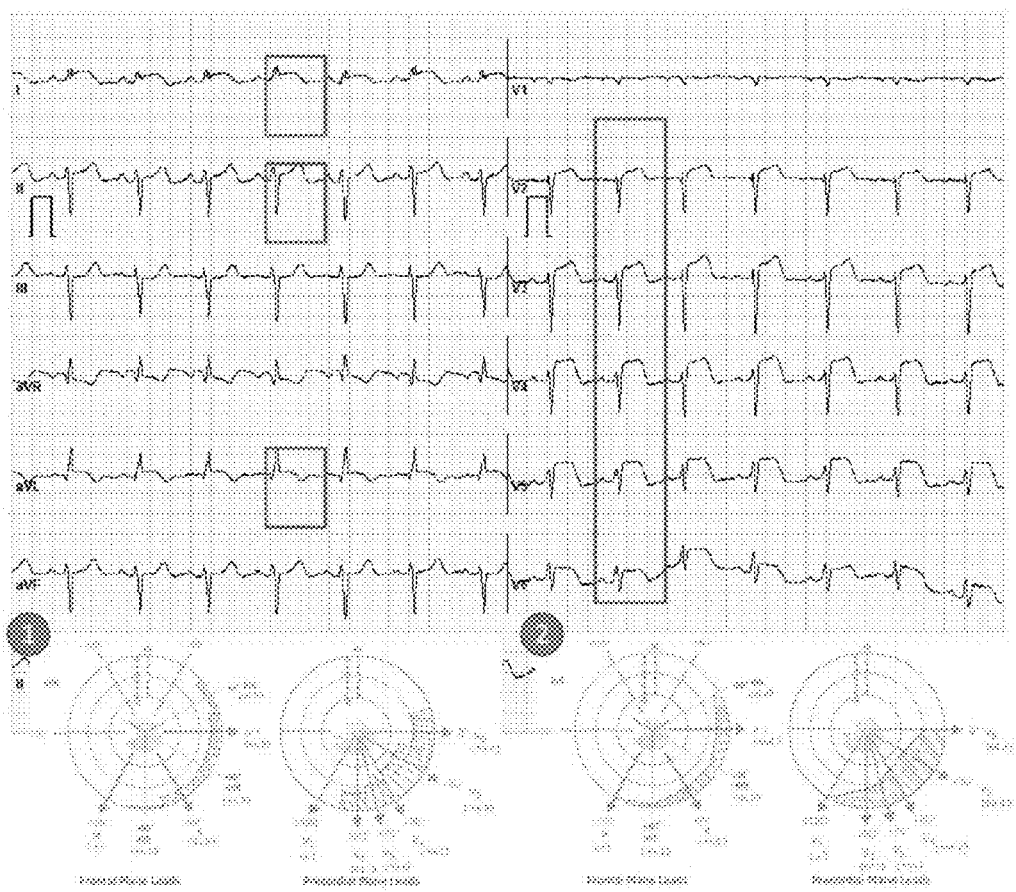
Figure 8:
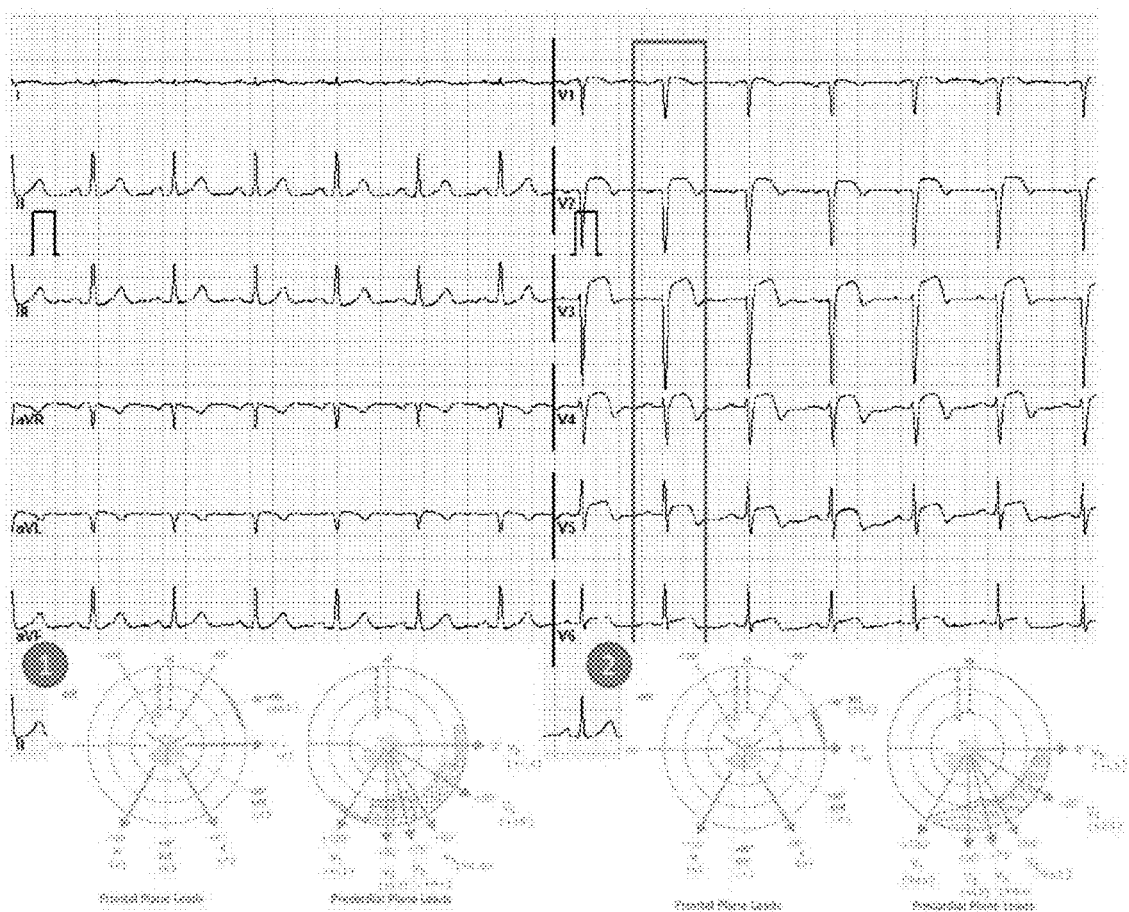
Figure 9:
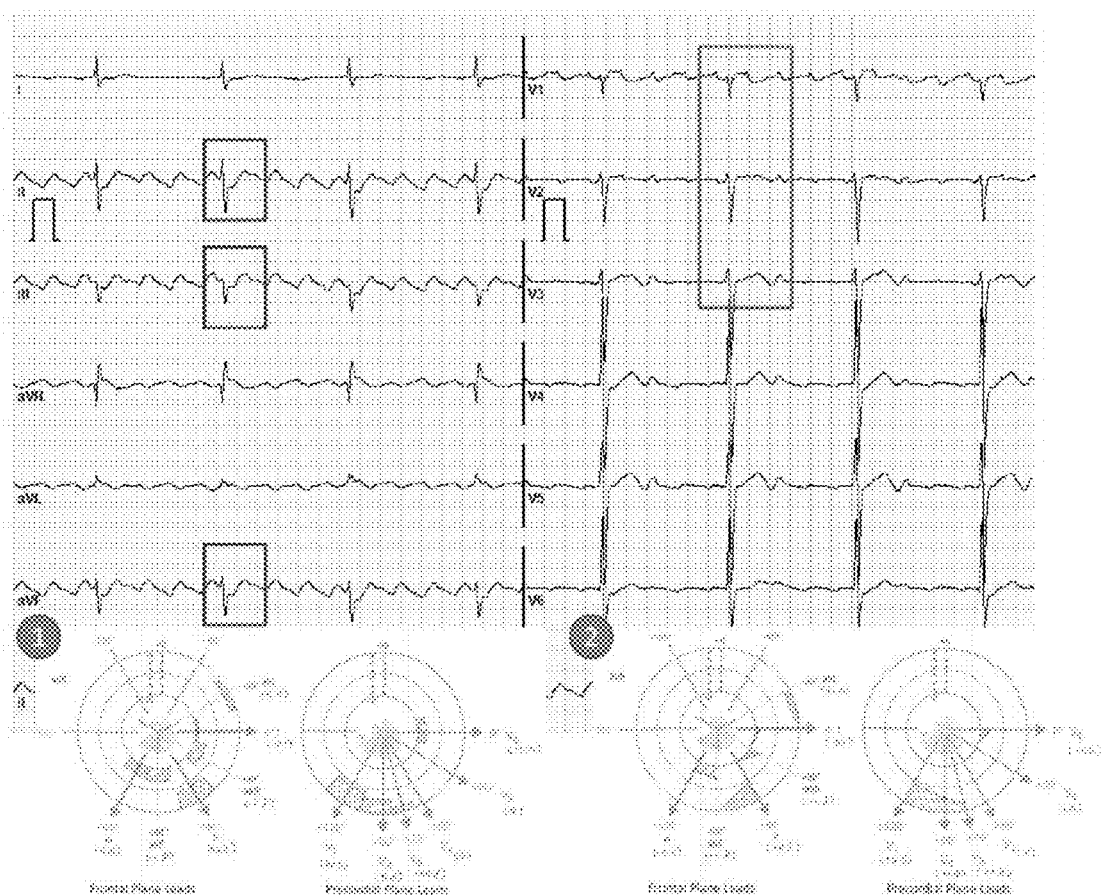
Figure 10:
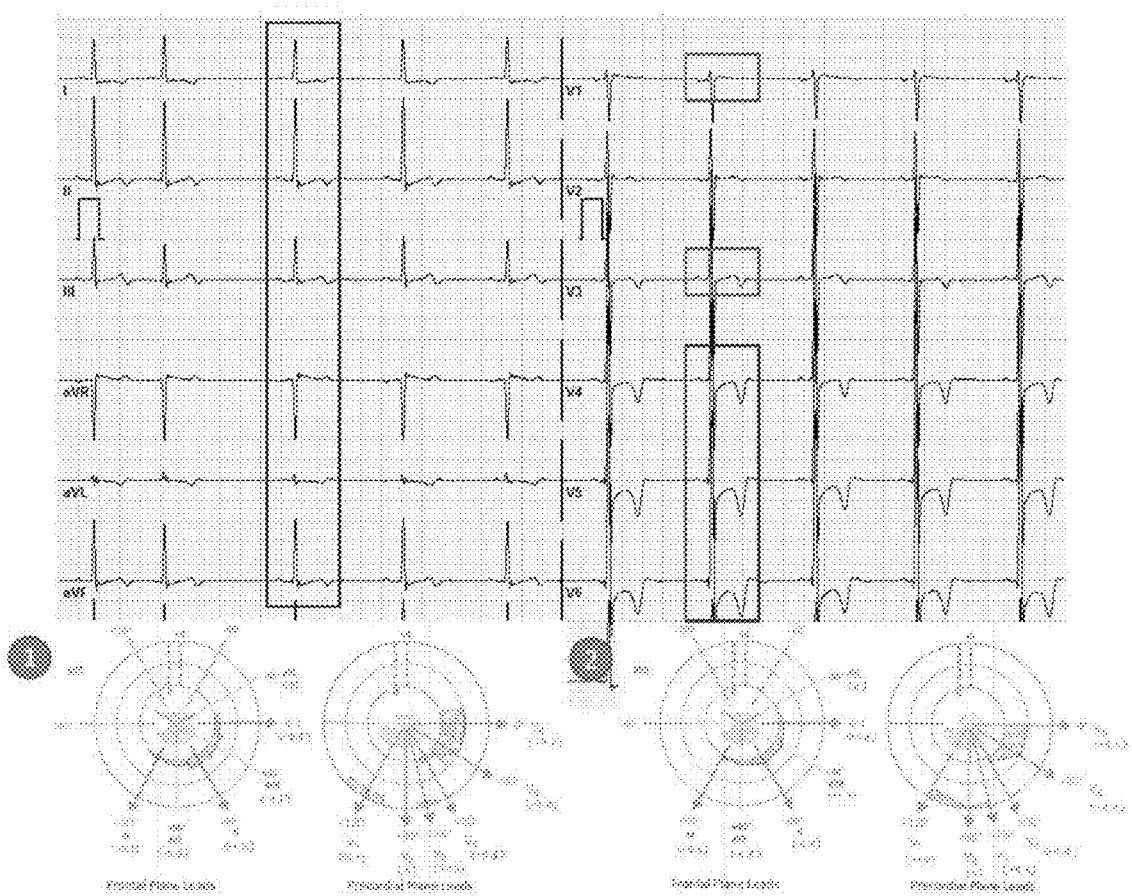
Figure 11:
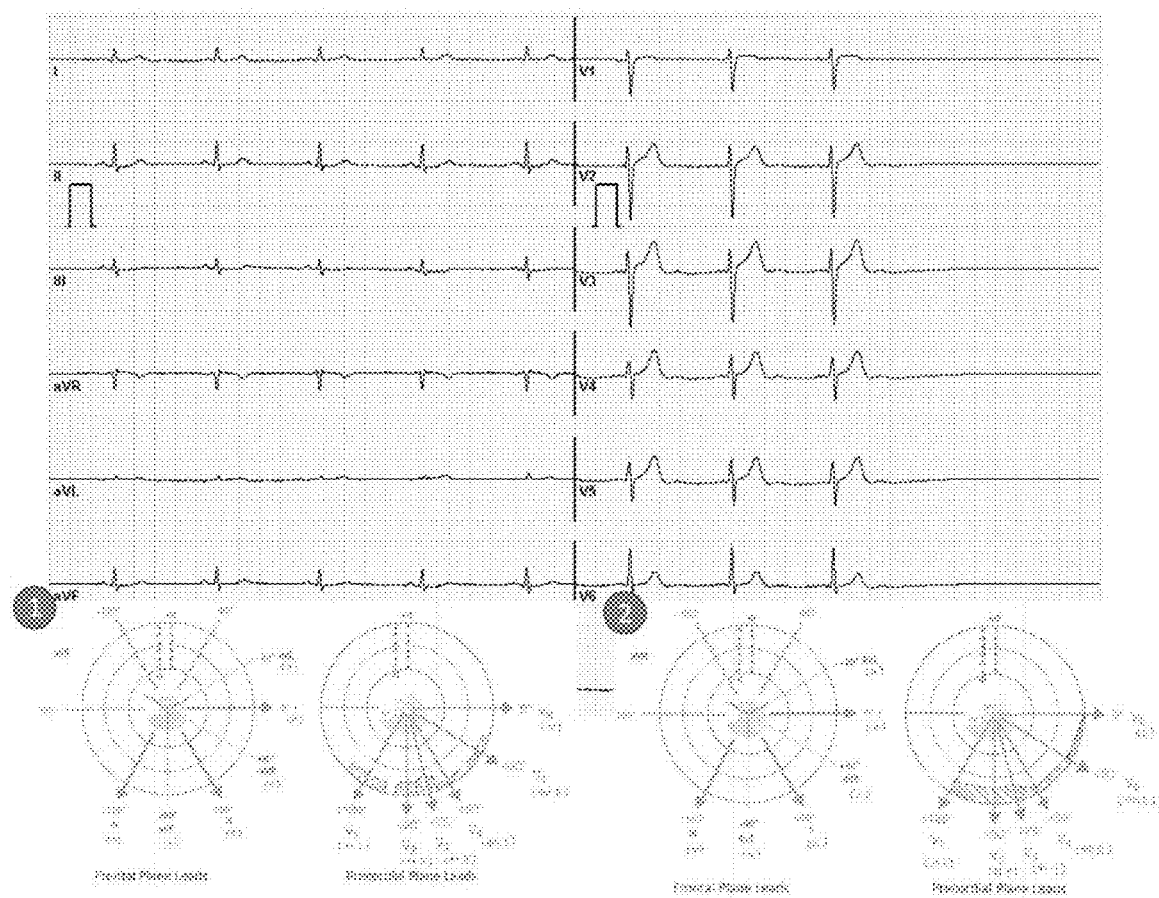

FIG. 4 is an explanatory diagram which shows a state of a method for displaying ECG data for the detection of myocardial ischemia according to a preferred embodiment of the present disclosure, in which the measured ECG values of limb leads (frontal plane leads; I to aVF) and chest leads (precordial plane leads; V1 to V6) are displayed by marking dots on the baseline followed by connecting each dot; and FIGS. 5 to 11 are explanatory diagrams which show various embodiments, with regard to subendocardial ischemia or transmural injury, of a method for displaying ECG data for the detection of myocardial ischemia according to a preferred embodiment of the present disclosure.

Referring to FIGS. 1 to 11, the method for displaying ECG data for the detection of myocardial ischemia is characterized in that a map is configured in the form of concentric circles using the ST segments obtained through electrocardiogram measurement. As shown in FIG. 2, the inner circle 100 consists of a "depression" origin and the outer circle 200 consists of an "elevation" origin wherein the measured ECG values of limb leads (frontal plane leads; I to aVF) and chest leads (precordial plane leads; V1 to V6) are displayed from the inner circle 100 in the case of "depression" while the measured ECG values of limb leads (frontal plane leads; I to aVF) and chest leads (precordial plane leads; V1 to V6) are displayed from the outer circle 200 in the case of "elevation", thereby making it possible for the user to intuitively confirm the presence of subendocardial ischemia or transmural injury of a patient through the map.

Additionally, in the present disclosure, the map is characterized in that five graduated rulers 300 are displayed in the form of concentric circles so as to enable the confirmation of the measured ECG values of limb leads (frontal plane leads; I to aVF) and chest leads (precordial plane leads; V1 to V6) between the inner circle 100 and the outer circle 200. As shown in FIG. 1, in the case of "depression", the map is configured to sequentially display the measured values from −1 to −6 from the next adjacent circle to the outer circle with the inner circle as the reference point; and in the case of "elevation", the map is configured to sequentially display the measured values from 1 to 6 from the next adjacent circle to the inner circle with the outer circle as the reference point. When displaying the measured ECG values of limb leads (frontal plane leads; I to aVF) and chest leads (precordial plane leads; V1 to V6) on the map, as shown in FIG. 3, each of the measured ECG values of limb leads (frontal plane leads; I to aVF) and chest leads (precordial plane leads; V1 to V6) can be displayed as a bar graph, and as shown in FIG. 4, it is also possible to mark dots on the baseline for the measured ECG values of limb leads (frontal plane leads; I to aVF) and chest leads (precordial plane leads; V1 to V6) and display them in a radial form by connecting each dot.

Meanwhile, as shown in FIGS. 5 to 11, it is possible to display various patient conditions in a bar graph or in a radial form. Since it is possible for the user to intuitively confirm, through a bar graph or an ST map displayed in a radial form, the possibility of subendocardial ischemia, the possibility of transmural injury, or the possibility of both subendocardial ischemia and transmural injury at the same time, the user does not have to manually check the ECG waveform as in the past, thus making it possible to promptly and accurately recognize the patient's condition and inducing rapid treatment.

Meanwhile, it is desirable that the map be configured such that each measured value is displayed under each lead name, which indicates the measured ECG values of limb leads (frontal plane leads; I to aVF) and chest leads (precordial plane leads; V1 to V6), and the measured ECG values of limb leads (frontal plane leads; I to aVF) and chest leads (precordial plane leads; V1 to V6) are configured to display each measured value under each lead name so as to make it easier for the user to check the measured value.

Meanwhile, the map is characterized in that it is configured to display the shape of the ventricle 400 inside the inner circle 100, and because of this, it is possible to intuitively confirm the location of subendocardial ischemia or transmural injury through the direction of the ventricle 400.

As described above, in the present disclosure, since a map is configured in the form of concentric circles using the ST segments obtained through ECG measurement such that the inner circle 100 consists of a "depression" origin and the outer circle 200 consists of an "elevation" origin to enable to display by connecting the graphs or dots according to the measured ECG values of limb leads (frontal plane leads; I to aVF) and chest leads (precordial plane leads; V1 to V6), it is possible to intuitively confirm the presence of subendocardial ischemia or transmural injury through the map, thus making it possible to promptly and accurately recognize the patient's conditions thereby inducing rapid treatment.

Most preferred embodiments have been disclosed in the drawings and specification. Although specific terms are used herein, they are used only for the purpose of illustrating the present disclosure, and not for the limitations of meanings or for the limitations of the scope of the present disclosure described in the claims. Therefore, those of ordinary skill in the art would be able to understand that various modifications and equivalent other embodiments are possible therefrom. Therefore, the true technical scope of the present disclosure should be determined by the technical ideas in the accompanying claims.

EXPLANATION OF REFERENCE NUMERALS

| 100: inner circle | 200: outer circle |
|---|---|
| 300: graduated ruler | 400: ventricle |

ADVANTAGEOUS EFFECTS OF THE INVENTION

As described above, according to the present disclosure, since a map is configured in the form of concentric circles using the ST segments obtained through ECG measurement such that the inner circle 100 consists of a "depression" origin and the outer circle 200 consists of an "elevation" origin to enable to display by connecting the graphs or dots according to the measured ECG values of limb leads (frontal plane leads; I to aVF) and chest leads (precordial plane leads; V1 to V6), it is possible to intuitively confirm the presence of subendocardial ischemia or transmural injury through the map. Therefore, the present disclosure has an advantage in that it is possible to promptly and accurately recognize the patient's state thereby inducing rapid treatment.

What is claimed is:

1. A method for displaying electrocardiogram (ECG) data on a display for the detection of myocardial ischemia, comprising:

measuring the ECG data using limb leads of the frontal plane of I to aVF and chest leads of the precordial plane of V I to V6;

processing the ECG data to determine ST segments having depression and elevation origins and values;

showing a plurality of graduated rulers in the form of concentric circles in between an inner concentric circle and an outer concentric circle; and creating a map on the display displaying the ST segments and values by plotting the depression values from −1 to −6 with the inner circle as the reference point and from the next adjacent circle toward the outer circle, and by plotting the elevation values from 1 to 6 with the outer circle as the reference point and from the next adjacent circle toward the inner circle.

2. The method of claim 1 further comprising:
configuring a bar graph according to the measured ECG values of limb leads (frontal plane leads; I to aVF) on the map and marking and connecting dots plotted for the chest leads (precordial plane leads; V1 to V6).

3. The method of claim 1 further comprising:
showing a shape of the ventricle inside the inner circle on the map.

4. The method of claim 3 further comprising:
Indicating each measured ECG values of limb leads (frontal plane leads; I to aVF) and chest leads (precordial plane leads; V1 to V6) under each lead name on the map.

5. A method for displaying electrocardiogram (ECG) data on a display for the detection of myocardial ischemia, comprising:

measuring the ECG data using limb leads of the frontal plane of I to aVF and chest leads of the precordial plane of V I to V6;

processing the ECG data to determine ST segments having depression and elevation origins and values; and creating a map on the display showing the ST segments and values indicating depression displaced from an inner concentric circle on the map on the monitor, and the ST segments and values indicating elevation are separately displaced from an outer concentric circle on the map on the display, wherein both the ST segments and values indicating depression and the ST segments and values indicating elevation are displaced on the display at the same time for simultaneous comparison and evaluation.

6. The method of claim 5 further comprising:
showing a plurality of graduated rulers in the form of one or more concentric circles in between the inner concentric circle and the outer concentric circle, wherein the depression values from −1 to −6 are plotted from the next adjacent circle to the outer circle with the inner circle as the reference point and the elevation points from 1 to 6 are plotted from the next adjacent circle to the inner circle with the outer circle as the reference point.

7. The method of claim 6 further comprising:
configuring a bar graph according to the measured ECG values of limb leads (frontal plane leads; I to aVF) on the map and
marking and connecting dots plotted for the chest leads (precordial plane leads; V1 to V6).

8. The method of claim 7 further comprising:
showing a shape of the ventricle inside the inner circle on the map.

9. The method of claim 8 further comprising:
Indicating each measured ECG values of limb leads (frontal plane leads; I to aVF) and chest leads (precordial plane leads; V1 to V6) under each lead name on the map.

10. A method for displaying electrocardiogram (ECG) data for the detection of myocardial ischemia, comprising:
measuring the ECG data using limb leads of the frontal plane of I to aVF and chest leads of the precordial plane of V I to V6;
processing the ECG data to determine ST segments having depression and elevation origins and values;
creating a map in the form of a plurality of concentric circles such that the map has an inner concentric circle that consists of the depression origin and an outer concentric circle that consists of the elevation origin; and
displaying the map on a display with the ST segments and values such that the ST segment values are displayed from the inner circle when the values indicate depression and from the outer circle when the values indicate elevation to detect myocardial ischemia from the displaced map, ST segments, and depression and elevation origins.

11. The method of claim 10 further comprising:
plotting the depression values from −1 to −6 are plotted from the next adjacent circle to the outer circle with the inner circle as the reference point and the elevation points from 1 to 6 are plotted from the next adjacent circle to the inner circle with the outer circle as the reference point.

12. The method of claim 11 further comprising:
configuring a bar graph according to the measured ECG values of limb leads (frontal plane leads; I to aVF) on the map and
marking and connecting dots plotted for the chest leads (precordial plane leads; V1 to V6).

13. The method of claim 12 further comprising:
showing a shape of the ventricle inside the inner circle on the map.

14. The method of claim 13 further comprising:
Indicating each measured ECG values of limb leads (frontal plane leads; I to aVF) and chest leads (precordial plane leads; V1 to V6) under each lead name on the map.

\* \* \* \* \*